(12) United States Patent
Prataprao Chavan et al.

(10) Patent No.: US 9,522,922 B2
(45) Date of Patent: Dec. 20, 2016

(54) PROCESS FOR THE PREPARATION OF INTERMEDIATE FOR THE PREPARATION OF OSELTAMIVIR PHOSPHATE

(71) Applicant: Council of Scientific and Industrial Research, Rafi Marg, New Delhi (IN)

(72) Inventors: Subhash Prataprao Chavan, Maharashtra (IN); Prakash Narsing Chavan, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 15/026,376

(22) PCT Filed: Oct. 7, 2014

(86) PCT No.: PCT/IN2014/000645
§ 371 (c)(1),
(2) Date: Mar. 31, 2016

(87) PCT Pub. No.: WO2015/049700
PCT Pub. Date: Apr. 9, 2015

(65) Prior Publication Data
US 2016/0222029 A1  Aug. 4, 2016

(30) Foreign Application Priority Data
Oct. 4, 2013 (IN) ............ 2956/DEL/2013

(51) Int. Cl.
C07C 211/36 (2006.01)
C07D 513/04 (2006.01)
C07D 233/32 (2006.01)
C07D 235/02 (2006.01)
C07C 269/04 (2006.01)
C07C 269/06 (2006.01)

(52) U.S. Cl.
CPC ........... C07D 513/04 (2013.01); C07C 211/36 (2013.01); C07C 269/04 (2013.01); C07C 269/06 (2013.01); C07D 233/32 (2013.01); C07D 235/02 (2013.01); *C07C 2101/16* (2013.01)

(58) Field of Classification Search
CPC ... C07D 513/04; C07D 233/32; C07D 235/02; C07C 211/36; C07C 2101/16
See application file for complete search history.

(56) References Cited

FOREIGN PATENT DOCUMENTS

| JP | 2008081489 | 4/2008 |
| WO | 2007099843 | 9/2007 |

OTHER PUBLICATIONS

Fukuta et al. "De Novo Synthesis of Tamiflu via a Catalytic Asymmetric Ring-Opening of meso-Azirdines with TMSN3." J. Am. Chem. Soc. vol. 128. (2006) pp. 6312-6313.
Morita et al. "A method for synthesis of an oseltamivir PET tracer", Bioorganic & Medicinal Chemistry Letters. vol. 18., (2008) pp. 600-602.

(Continued)

Primary Examiner — Matthew Coughlin
(74) Attorney, Agent, or Firm — Merchant & Gould P.C.

(57) ABSTRACT

The present invention discloses an economic, simple, azide and aziridine complexity free process for the synthesis of osletamivir phosphate (Tamiflu) by stereospecific amidoalkylation of imidazothiazolone from easily available L-cysteine via Ramberg-Backlund reaction and Sharpless-Reich protocol.

3 Claims, 3 Drawing Sheets

(56) References Cited

OTHER PUBLICATIONS

Chavan et al. "Diastereoselective Amidoalkylation of (3S,7aR)-6-Benzyl-7-hydroxy-3-phenyltetra-hydro-5H-imidazo [1,5-c][1,3]thiazol-5-one: A short highly efficient Synthesis of (+)-Biotin." J. Org. Chem. vol. 70 (2005) 1901-1903.
International Search Report for International Application No. PCT/IN2014/000645 mailed Feb. 10, 2015, 3 pages.

PROCESS FOR THE PREPARATION OF INTERMEDIATE FOR THE PREPARATION OF OSELTAMIVIR PHOSPHATE

This application is a National Stage Application of PCT/IN2014/000645, filed 7 Oct. 2014, which claims benefit of Serial No. 2956/DEL/2013, filed 4 Oct. 2013 in India and which applications are incorporated herein by reference. To the extent appropriate, a claim of priority is made to each of the above disclosed applications.

FIELD OF THE INVENTION

The present invention relates to an economic, simple, azide and aziridine complexity free process for the synthesis of osletamivir phosphate (Tamiflu). Particularly, the present invention relates to process for the synthesis of osletamivir phosphate (Tamiflu) by stereospecific amidoalkylation of imidazothiazolone from easily available L-cysteine via Ramberg-Backlund reaction and Sharpless-Reich protocol.

BACKGROUND AND PRIOR ART OF THE INVENTION

Influenza, commonly referred to as flu, is an infectious disease caused by RNA viruses of the family Orthomyxoviridae (the influenza viruses). Influenza spreads around the world in seasonal epidemics, resulting in the deaths of between 200,000 and 500,000 to people every year, up to millions in some pandemic years. The development of effective antiviral medicines is hampered by the exceptionally high mutation rates of influenza virus. Therefore, in order to be successful, new drugs should target the molecular mechanisms specific to the proliferation of the virus.

Figure 1:
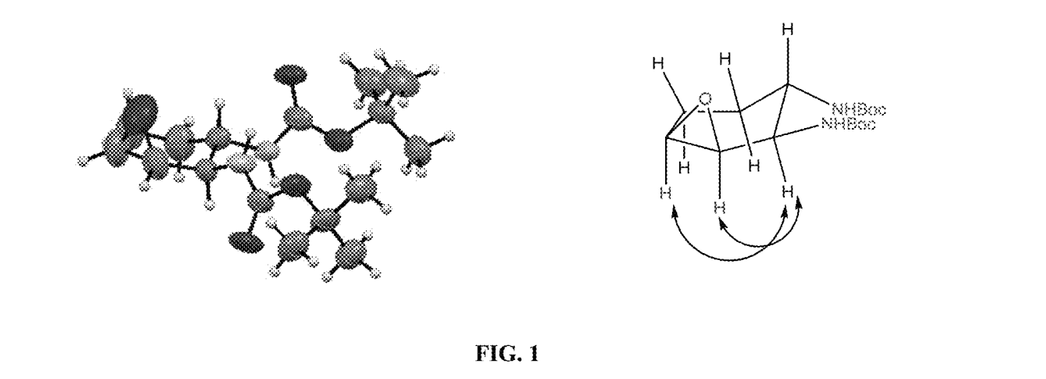
FIG. 1 depicts ORTEP diagram and nOe-mult of epoxide 11.

H5N1 and H1N1 strains of virus have shown pandemic disease threat worldwide and has been the cause of death of thousands of people till date by viral flu. These viruses actually cut surface protein of infected host cell and allow spreading to other cell. Oseltamivir phosphate (1, Tamiflu, Ro 64-0796, GS4104) and Zanamivir (2, Relenza, GG 167) are currently used as neuraminidase inhibitor drugs. Oseltamivir phosphate is recommended as the best choice due to its oral active form and bioavailability (FIG. 1). The anti-influenza drug 1 was initially discovered by Gilead Sciences and subsequently licensed to Roche for production from (−)-shikimic acid. It has inevitably increased the demand of tamiflu due to threat of avain and seasonal influenzas. There is huge pressure on raw materials supply to meet worldwide demand of tamiflu.

Tamiflu (1)

Relenza (2)

Currently manufacturing process for tamiflu uses (−)-shikimic acid as the raw material. The insufficient quantities of (−)-shikimic acid either by extraction from its natural sources, fermentation or chemical synthesis is a drawback in meeting the demands. Thus far the unabated efforts of chemical community have devised many alternative syntheses of seemingly simple but synthetically challenging molecule tamiflu, utilizing readily available and inexpensive starting materials. There is still requirement of the synthesis of 1, where the use of azide and aziridine intermediate should be avoided to minimize the hazard and complexity in the synthesis.

Article titled "Two approaches toward the formal total synthesis of oseltamivir phosphate (Tamiflu): catalytic enantioselective three-component reaction strategy and L-glutamic acid strategy" by K Alagiri et al. published in *J Org Chem*, 2013 Apr. 19, 78(8):4019-26 reports two independent formal total syntheses of oseltamivir phosphate were successfully achieved: the first utilized a copper-catalyzed asymmetric three-component reaction strategy, and the second utilized L-glutamic acid γ-ester as a chiral source to install the correct stereochemistry. Both strategies used Dieckmann condensation to construct a six-membered ring core, after which manipulation of the functional groups and protecting groups accessed Corey's intermediate for the synthesis of oseltamivir phosphate. While the first synthesis was accomplished via four purification steps in 25.7% overall yield, albeit with moderate optical purity (76% ee), the second strategy achieved the synthesis via six purification steps in 19.8% overall yield with perfect enantiocontrol.

Article titled "Efficient Formal Synthesis of Oseltamivir Phosphate (Tamiflu) with Inexpensive d-Ribose as the Starting Material" by H Osato et al. published in *Org. Lett.*, 2010, 12 (1), pp 60-63 reports an efficient formal synthesis of oseltamivir phosphate (Tamiflu) has been achieved in 12 steps with use of the inexpensive and highly abundant d-ribose as the starting material. This concise alternative route does not utilize protecting groups and features the introduction of 3-pentylidene ketal as the latent 3-pentyl ether, the use of a highly efficient RCM reaction to form the Tamiflu skeleton, and selective functional group manipulations.

Article titled "A Practical and Azide-Free Synthetic Approach to Oseltamivir from Diethyl d-Tartrate" by J Weng et al. published in *J. Org. Chem.*, 2010, 75 (9), pp 3125-3128 reports a short and practical synthesis of oseltamivir was accomplished in 11 steps from inexpensive and abundant diethyl d-tartrate starting material. This azide-free route featured an asymmetric aza-Henry reaction and a domino nitro-Michael/Horner-Wadsworth-Emmons (HWE)

reaction as the key steps to construct the relevant cyclohexene ring of the product, which provided an economical and practical alternative for the synthesis of oseltamivir.

Article titled "Ring-closing metathesis-based synthesis of (3R,4R,5S)-4-acetylamino-5-amino-3-hydroxy-cyclohex-1-ene-carboxylic acid ethyl ester: a functionalized cycloalkene skeleton of GS4104" by X Cong et al. published in *J Org Chem*, 2006 Jul. 7; 71(14), 5365-8 reports (3R,4R,5S)-4-Acetylamino-5-amino-3-hydroxy-cyclohex-1-ene-carboxylic acid ethyl ester, a functionalized cyclohexene skeleton of GS4104, was diastereoselectively synthesized. A major advantage of this synthesis is the use of readily available L-serine to replace frequently used (−)-shikimic acid or (−)-quinic acid as the starting material. Ring-closing metathesis and diastereoselective Grignard reactions successfully served as the key steps. Absolute configurations of the key intermediates were confirmed by corresponding two-dimensional NMR studies.

Article titled "Novel asymmetric synthesis of oseltamivir phosphate (Tamiflu) from (−)-shikimic acid via cyclic sulfite intermediates" by L D Nie et al. published in *Tetrahedron: Asymmetry*, Volume 22, Issues 16-17, 15 Sep. 2011, Pages 1692-1699 reports a novel asymmetric synthesis of oseltamivir phosphate 1 from the naturally abundant (−)-shikimic acid via 3,4-cyclic sulfite intermediate 3 (FIG. 2) is described. Target compound 1 was obtained in 39% overall yield from this nine-step synthesis, and the characteristic step of the synthesis is the regio- and stereospecific nucleophilic substitution with sodium azide at the allylic (C-3) position of 3,4-cyclic sulfite 3. Since the yield of the direct-aziridine-formation from the unprotected dihydroxyl azide 4 was not satisfactory, two improved preparations of the established compound 7 via protected 3,4-cyclic sulfites 10 and 13 (FIG. 3) have been developed. In these two improved preparations, compound 7 was obtained from 3,4-cyclic sulfite 3 in 7-steps in 64% or 62% overall yield, respectively.

OBJECTIVE OF INVENTION

The main objective of the present invention is to provide a process for the preparation of oseltamivir phosphate (tamiflu) by stereospecific amidoalkylation of imidazothiazolone from available L-cysteine via Ramberg-Backlund reaction and Sharpless-Reich protocol.

SUMMARY OF THE INVENTION

Accordingly, present invention provides a process for the preparation of intermediate for the preparation of oseltamivir phosphate comprising the steps of:
a) providing allyl compound A from cysteine by known method;

A b) adding Zinc dust and saturated aq. solution of ammonium chloride to a solution of allyl compound A of step (a) in tetra hydro furan (THF) to obtain the reaction mixture;
c) refluxing the reaction mixture as obtained in step (c) to obtain thiol compound 5;

5 d) stirring the crude thiol 5 of step (c) at room temperature in the range of 25-30° C. in water to afford seven membered cyclic sulphide 7.

7 e) oxidising sulphide 7 of step (d) at room temperature in the range of 25-30° C. by oxone to afford sulfone 8;

8 f) subjecting sulfone 8 of step (e) to Ramberg-Backlund reaction to furnish the cyclohexene urea 4;

4 g) reducing urea 4 of step (f) with LAH to furnish imidazolidine and subjecting imidazolidine without purification to hydrolysis in 1% HCl to afford corresponding crude vicinal diamine;

h) masking the crude diamine of step (g) as its carbamate derivative with neat Boc anhydride to afford diboc 9;

9 i) subjecting compound 9 of step (h) to debenzylation under Birch conditions to obtain debenzylated compound 10;

10 j) epoxidation of compound 10 of step (i) furnished α-carbamate directed stereospecific epoxide 11 as a single diastereomer;

11 k) rearranging epoxide 11 of step (j) to allylic alcohol 12 in one pot two steps protocol without isolation of the intermediate;

12 l) DMP oxidation of allylic alcohol 12 of step (k) on DMP in DCM afforded α, β-unsaturated ketone 3 intermediate for the preparation of oseltamivir phosphate.

In an embodiment of the present invention, refluxing in step (c) is carried for 6 to 7 hrs.

In another embodiment of the present invention, stirring in step (d) is carried for 4 to 5 hrs.

DETAILED DESCRIPTION OF THE INVENTION

Figure 3:
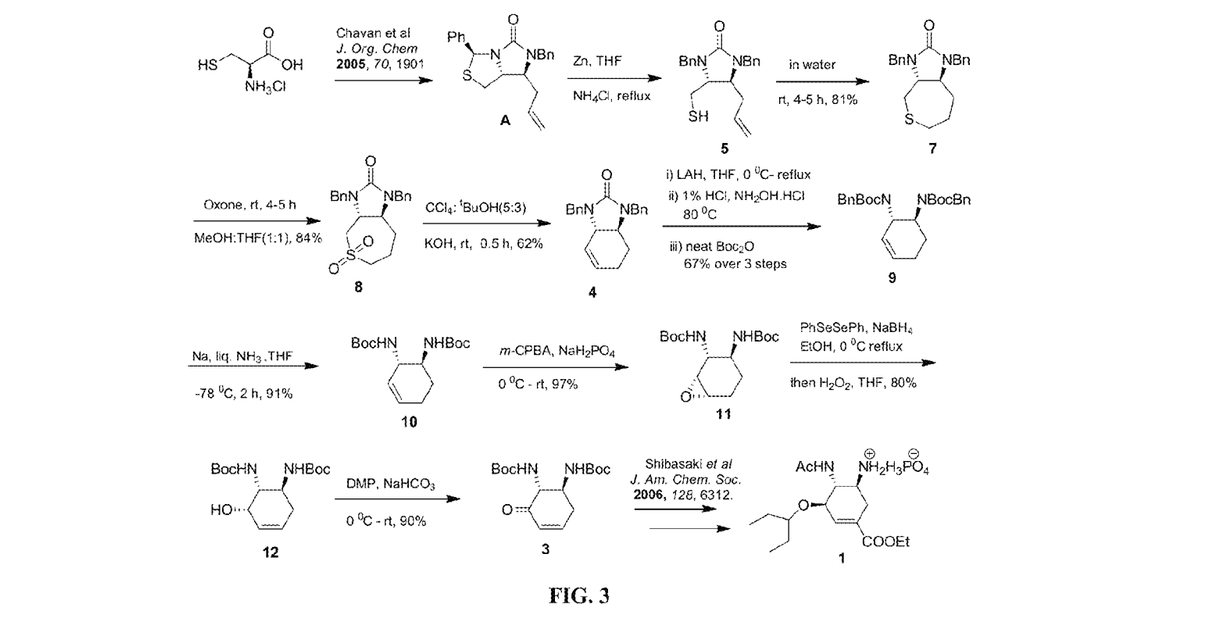
FIG. 3 represents steps involved in synthesis of compound of formula 1.
Figure 4:
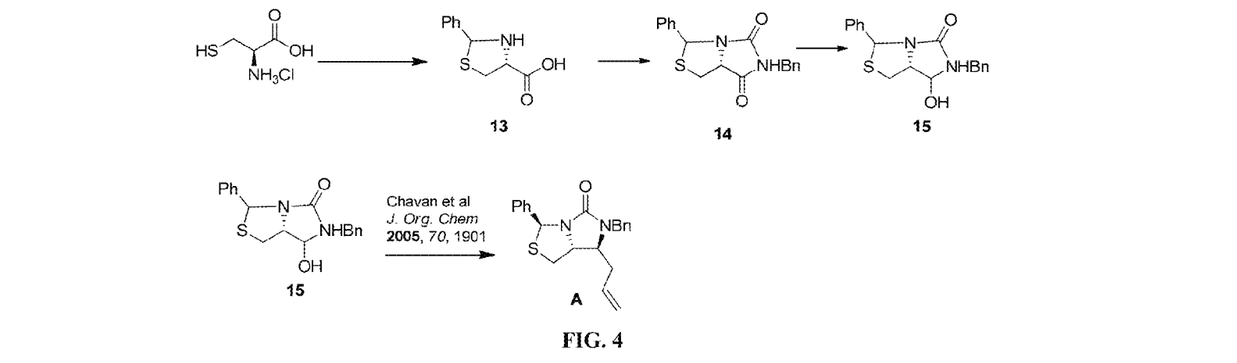
FIG. 4 represents preparation of compound A from L-cysteine as reported in Chavan et al, *J. Org. Chem.* 2005, 70, 1901.
Figure 5:
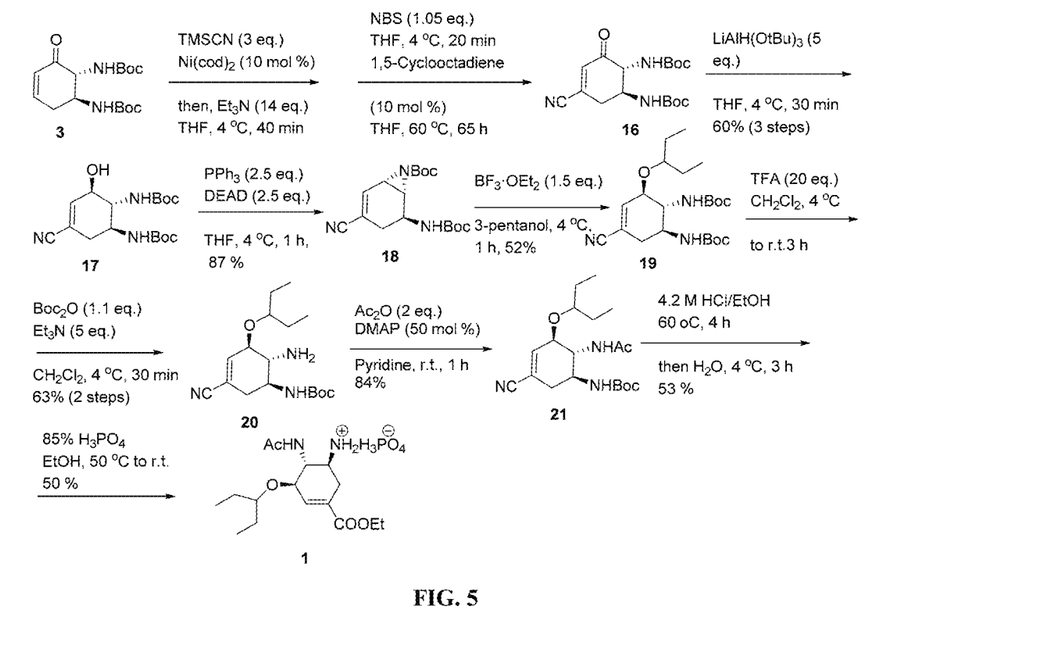
FIG. 5 represents preparation of compound 1 starting from compound 3 as reported in Shibasaki et al; *J. Am. Chem. Society*, 2006, 128, 6312.

The present invention provide an economic, simple, azide and aziridine complexity free process for the preparation of oseltamivir phosphate (tamiflu) by stereospecific amidoalkylation of imidazothiazolone from abundant, inexpensive and easily available L-cysteine via Ramberg-Backlund reaction and Sharpless-Reich protocol (FIG. 3).

In an aspect, the present invention also provide a process for the preparation of (3aR,8aS)-1, 3-Dibenzylhexahydro-1H-thiepino[3, 4-d]imidazol-2(3H)-one form L-cysteine.

The present invention provides a process for the synthesis of compound Di-tert-butyl ((1S, 2R)-3-oxocyclohex-4-ene-1, 2-diyl)dicarbamate of formula 3

Figure 2:
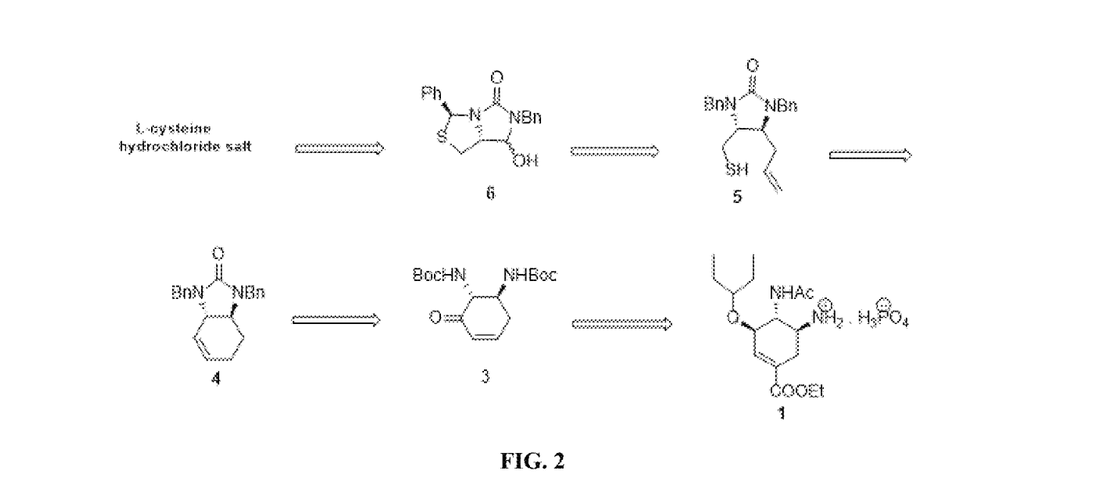
FIG. 2 represents retro synthesis of compound 1.

3 comprising the steps of:
a, subjecting L-cysteine hydrochloride salt through intermediate 6 to obtain thiol 5;
b. subjecting thiol 5 of step (a) to intramolecular thiol cyclization and Ramberg-Backlund reaction to obtain cyclohexene compound 4;
c. Urea hydrolysis, Birch reduction, epoxidation and regiospecific epoxide opening followed by oxidation of cyclohexene compound 4 of step (b) afforded the key intermediate enone 3. The process is depicted in FIG. 2.

The present invention provides a process for the synthesis of compound (3aR,8aS)-1, 3-Dibenzylhexahydro-1H-thiepino[3, 4-d]imidazol-2(3H)-one of formula 7,

7 comprising the steps:
a. Adding Zinc dust and saturated aq. solution of ammonium chloride to a solution of allyl compound A in THF to obtain the reaction mixture;
b. Refluxing the reaction mixture of step (a) and monitoring the completion of reaction by TLC;
c. Filtering the reaction mixture of step (b) through celite and washing the celite with ethyl acetate to obtain the filtrate;
d. Work-up of the filtrate of step (c) to give thiol 5;
e. Stirring the crude thiol 5 of step (d) at rt in water and monitoring the completion of reaction by TLC followed by extraction and workup to afford seven membered cyclic sulphide 7 (16.20 g, 81%) as colourless liquid;

f. Oxidising sulphide 7 of step (e) by oxone to afford sulfone 8;

g. Subjecting sulfone 8 of step (f) to Ramberg-Backlund reaction to furnish the cyclohexene urea 4;

h. Reducing urea 4 of step (g) with LAH to furnish imidazolidine and subjecting imidazolidine without purification to hydrolysis in 1% HCl to afford corresponding crude vicinal diamine;

i. Masking the crude diamine of step (h) as its carbamate derivative with neat Boc anhydride to afford diboc 9;

j. Subjecting compound 9 of step (i) to debenzylation under Birch conditions to obtain debenzylated compound 10;

k. Epoxidation of compound 10 of step (j) furnished α-carbamate directed stereospecific epoxide 11 as a single diastereomer;

l. Rearranging epoxide 11 of step (k) to allylic alcohol 12 in one pot two steps protocol without isolation of the intermediate;

m. DMP oxidation of allylic alcohol 12 of step (l) on DMP in DCM afforded α, β-unsaturated ketone 3.

EXAMPLES

Following examples are given by way of illustration therefore should not be construed to limit the scope of the invention.

Example 1 to 4

Chavan et al, J. Org. Chem. 2005, 70, 1901

Example 1

(4R)-2-phenylthiazolidine-4-carboxylic acid (13)

To a solution of L-cysteine hydrochloride hydrate (60 g, 0.34 mol), in water (525 mL) was added potassium acetate (36 g, 0.37 mol) was added and allowed to stir till a solution was obtained. To this solution 95% of methanol (525 mL) was added followed by immediate addition of benzaldehyde (44.2 g, 0.42 mol) in one portion. The reaction mixture was kept at 25° C. for 3 h and an additional 3 h at 0° C. The product formed as a solid was filtered, washed with methanol, and dried to afford 3 as a white solid. Yield: 72.0 g (98%).

Example 2

(3S,7aR)-6-Benzyl-3-phenyl perhydroimidazo[1,5-c][1,3]thiazol-5,7-dione (14)

In a 500 mL two-necked round bottom flask filled with nitrogen, (20.0 g, 95.6 mmol) thiazolidine carboxylic acid 13 was placed in 150 mL of anhydrous THF. To this suspension, a solution of (15.2 g, 1.143 mol) benzyl isocyanate in 50 mL of THF was added dropwise over a period of 20 min. The reaction mixture was stirred for 1 h at 60° C. The reaction mixture was then cooled to 0° C. and concd HCl (20.0 mL) was added and the reaction mixture was allowed to stir for 90 min at 60° C. Then the reaction mixture was allowed to cool to room temperature (27° C.), water was added and extracted with ethyl acetate (3×200 mL). The combined organic layers were dried over anhydrous Na$_2$SO$_4$ filtered and concentrated under reduced pressure. After triturating with methanol the hydantoin 4 was obtained as a white crystalline solid 27.8 g, (90%).

Example 3

(3S,7aR)-6-Benzyl-7-hydroxy-3-phenyltetrahydro-5H-imidazo[1,5-c][1,3]thiazol-5-one (15)

The imidazolidinone 14 (32.4 g, 0.1 mmol) was taken in aqueous THF or methanol (300 mL) and cooled to 0° C. Sodium, borohydride (5.6 g, 0.15 mol) was added gradually in small portions over a period of time (30 min). After addition of sodium borohydride was complete, the reaction mixture was brought to room temperature (25° C.) and stirring continued for additional half an hour. The reaction mixture was then quenched with water and the contents were extracted with ethyl acetate. The combined layers were washed with water (100 mL), brine (100 mL) and dried over anhydrous $Na_2SO_4$ and filtered. After concentration under reduced pressure a white crystalline solid of hydroxy imidazothiazolone, this was sufficiently pure. Yield: 32.5 g (99%).

Example 4

(3S,7S,7aR)-7-Allyl-6-benzyl-3-phenyltetrahydro-5H-imidazo[1,5-c][1,3]thiazol-5-one (A)

To (5 g) of 15 (1 mmol) in dichloromethane (10 mL) was added TMS allyl (1.2 mmol) and the solution was cooled and stirred at 0° C. Boron trifluoride etherate ($BF_3.OEt_2$) (1.1 mmol) was added drop wise. The reaction mixture was stirred at 0° C. for 10 min. and quenched with saturated ammonium chloride (10 mL) The organic layer was separated, dried over anhyd. $Na_2SO_4$. Concentration under reduced pressure and column purification ($SiO_2$) with ethyl acetate:pet.ether (15:85) provided 7-substituted imidazothiazolones (compound A) as viscous liquid in near quantitative yield.

Example 5 to 12

Preparation of Intermediate (3) for the Preparation of Oseltamivir Phosphate (1)

Example 5

(3aR, 8aS)-1, 3-Dibenzylhexahydro-1H-thiepino-[3,4-d]-imidazol-2(3H)-one (7)

To a solution of allyl compound A (20 gm, 57.14 mmol) in THF (200 mL) was added zinc dust (111 gm, 1.74 mol) and saturated aq solution of ammonium chloride (200 mL). The reaction mixture was refluxed at 80° C. for 6-7 h, completion of reaction was monitored by TLC. The reaction mixture was filtered through celite and the celite was washed with ethyl acetate (2×100 mL). The filtrate was washed with 10% HCl (100 mL) and compound was extracted with ethyl acetate (3×100 mL). The combined organic layer was dried over anhydrous $Na_2SO_4$, filtered and concentrated under reduced pressure to furnish thiol 5. [(4S,5R)-4-allyl-1,3-dibenzyl-5-(mercaptomethyl)imidazolidin-2-one].

The crude thiol 5 (20.00 g, 56.74 mmol) was stirred at rt in water (100 mL) for 4-5 h. After completion of reaction monitored by TLC, compound was extracted with ethyl acetate (3×100 mL). The combined organic layer was dried over anhydrous $Na_2SO_4$, filtered and concentrated under reduced pressure to furnish a residue which was purified by column chromatography over flash silica gel, eluting with 10% ethyl acetate in pet ether as the eluent to afford seven membered cyclic sulphide 7 (16.20 g, 81%) as colourless liquid.

IR ($CHCl_3$, $cm^{-1}$): vmax 3030, 1709, 1604, 1447, 1029.

HRMS: observed—375.1497 calculated—375.1502.

$^1$H NMR (400 MHz, $CDCl_3$+$CCl_4$) δ 7.35-7.25 (m, 10H), 4.76 (d, J=16 Hz, 1H), 4.67 (d, J=16 Hz, 1H), 4.22 (d, J=16 Hz, 1H), 4.18 (d, J=16 Hz, 1H), 3.27-3.22 (m, 2H), 2.97 (dd, J=12, 4 Hz, 1H), 2.60-2.53 (m, 1H), 2.58-2.54 (m, 1H), 2.26 (dd, J=12, 8 Hz, 1H), 2.12-2.15 (m, 1H), 1.96-1.93 (m, 1H), 1.78-1.71 (m, 1H), 1.43-1.36 (m, 1H).

$^{13}$C NMR (100 MHz, $CDCl_3$+$CCl_4$) δ 161.00, 137.21, 128.83, 128.79, 128.27, 128.23, 127.67, 127.59, 62.57, 59.05, 46.64, 46.13, 32.16, 29.98, 28.99, 28.36.

Example 6

(3aR, 8aS)-1, 3-Dibenzylhexahydro-1H-thiepino[3,4-d]imidazol-2(3H)-one 5, 5 dioxide (8)

To a solution of sulfide 7 (10.00 gm, 28.37 mmol) in THF:MeOH(1:1) was added oxone (52 gm, 81.11 mmol) in water (100 mL). After stirring at room temperature (30° C.) for 4-h, the reaction mixture was filtered through celite and celite was washed thoroughly with methanol (3×60 mL). Filtrate was concentrated under reduced pressure and water (100 mL) was added to the residue. Compound was extracted with ethyl acetate (3×100 mL). The combined organic layer was dried over anhydrous sodium sulphate, filtered and concentrated under reduced pressure to furnish crude residue. The residue was purified by column chromatography over silica gel with 30% ethyl acetate in pet. ether as an eluent to afford compound 8 (9.16 gm, 84%) as a white solid.

$R_f$: 0.3 (Pet. ether-ethyl acetate, 50:50)

MF: $C_{21}H_{24}N_2O_3S$, MW: 384.49

$[\alpha]_D^{25}$: +49.09 (c 1.1, $CHCl_3$)

IR ($CHCl_3$, $cm^{-1}$): vmax 2924, 1704, 1602, 1450, 1170.

MP: 155-157° C.

$^1$H NMR (200 MHz, $CDCl_3$+$CCl_4$): δ 7.42-7.22 (m, 10H), 4.76 (d, J=16 Hz, 1H), 4.67 (d, J=16 Hz, 1H), 4.22 (d, J=12 Hz, 1H), 4.15 (d, J=12 Hz, 1H), 3.60-3.22 (m, 3H), 3.08-2.83 (m, 3H), 2.33-1.87 (m, 3H), 1.50-1.33 (m, 1H)

$^{13}$C NMR (125 MHz, $CDCl_3$+$CCl_4$): δ 160.2, 136.3, 135.9, 136.1, 128.9, 128.8, 128.1, 127.9, 127.8, 127.7, 77.1, 58.7, 58.4, 54.5, 53.4, 46.6, 46.0, 29.6, 18.7.

HRMS: observed—407.1398, calculated—407.1400.

Example 7

(3aS, 7aS)-1, 3-Dibenzyl-3, 3a, 7, 7a-tetrahydro-1H-benzo[d]imidazol-2(6H)-one (4)

To a solution of sulfone 8 (3.00 gm, 7.80 mmol) in CCl$_4$:t-BuOH(40 mL, 5:3) was added potassium hydroxide flakes (660 mg, 11.71 mmol) and the reaction mixture was stirred at room temperature (27° C.) for 0.5 h. The reaction mixture was concentrated under reduced pressure, and saturated solution of ammonium chloride was added to the residue. Compound was extracted with ethyl acetate (3×50 mL). The combined organic layer was dried over anhydrous Na$_2$SO$_4$, filtered and concentrated under reduced pressure to obtain residue, which was purified by column chromatography over silica gel with 5% ethyl acetate in pet ether as an eluent to give compound 4 (1.54 gm, 62%) as a white solid.

R$_f$: 0.5 (Pet ether-ethyl acetate, 80:20).
MF: C$_{21}$H$_{22}$N$_2$O, MW: 318.42.
$[\alpha]_D^{25}$: +30.0 (c 0.4, CHCl$_3$).
IR (CHCl$_3$, cm$^{-1}$): vmax 2925, 1704, 1629, 1495, 1238.
MP: 75-77° C.
$^1$H NMR (500 MHz, CDCl$_3$+CCl$_4$): δ 7.39-7.23 (m, 33H), 5.74 (dd, J=1.7, 9.9 Hz, 2H), 5.49-5.41 (m, 2H), 4.57 (d, J=15 Hz, 1H), 4.50 (d, J=15 Hz, 1H), 4.43 (d, J=15 Hz, 1H), 4.39 (d, J=15 Hz, 1H), 3.43-3.37 (m, 1H), 3.01-2.93 (m, 1H), 2.26-2.04 (m, 2H), 1.94-1.85 (m, 1H), 1.52-1.41 (m, 1H).
$^{13}$C NMR (125 MHz, CDCl$_3$+CCl$_4$): δ 164.0, 137.6, 137.2, 128.6, 128.5, 128.3, 127.6, 127.5, 127.4, 127.3, 124.0, 59.0, 58.7, 47.4, 47.2, 25.2, 24.56.
HRMS: Observed—341.1619, calculated—341.1624.

Example 8

Di-tert-butyl (1S, 2S)-cyclohex-3ene-1, 2-diylbis(benzylcarbamate) (9)

To a cooled solution of olefin 4 (1.2 gm, 3.77 mmol) in dry THF at 0° C. was added lithium aluminium hydride portionwise (715 mg, 18.84 mmol). The reaction mixture was stirred at room temperature (25° C.) for 30 min and was quenched by addition of 15% NaOH solution and ice pieces. Then anhydrous Na$_2$SO$_4$ was added to the reaction and stirred for 10 min. The resultant solution was filtered and the residue was washed with the ethyl acetate (2×15 mL). The filterate was concentrated under reduced pressure. Crude compound was directly subjected for further reaction without purification.

The crude compound (1.15 gm) was subjected to hydrolysis by treatment with aq 1% HCl (10 mL) and NH$_2$OH.HCl (3.5 gm, excess) and heating at 80° C. for 1 h. The reaction mixture was neutralised with solid NaHCO$_3$ and compound was extracted with DCM (3×15 mL) The organic layer was dried over anhydrous Na$_2$SO$_4$, filtered and concentrated under reduced pressure to obtain crude diamine.

The crude diamine (1.1 gm) without purification was chemically masked with neat (Boc)$_2$O (1.93 mL, 11.30 mmol) and cat. DMAP (100 mg). The reaction mixture was stirred at room temperature (30° C.) for 3 h, water was added and the compound was extracted with DCM (3×15 mL). The combined organic layer was dried over anhydrous Na$_2$SO$_4$, filtered and concentrated under reduced pressure to furnish a residue which was purified by column chromatography over silica gel, eluting with 5% ethyl acetate in pet ether as an eluent to afford compound 9 (1.54 gm, 67% over three steps) as a colourless syrup.

R$_f$: 0.7 (Pet ether:ethyl acetate, 80:20).
MF: C$_{30}$H$_{40}$N$_2$O$_4$, MW: 492.66.
Yield: 67% (over three steps).
$[\alpha]_D^{25}$: +6.0 (c 2.0, CHCl$_3$).
IR (CHCl$_3$, cm$^{-1}$) v$_{max}$ 2924, 1695, 1603, 1365, 1165.
$^1$H NMR (400 MHz, CDCl$_3$+CCl$_4$): □ 7.48-7.04 (m, 10H), 5.93-5.31 (m, 2H), 5.26-3.27 (m, 6H), 2.40-1.74 (m, 4H), 1.59-1.22 (m, 18H).
$^{13}$C NMR (125 MHz, CDCl$_3$+CCl$_4$): δ 156.2, 155.7, 140.6, 129.5, 128.8, 128.2, 128.0, 127.8, 127.3, 126.5, 126.4, 126.2, 79.6, 79.5, 58.6, 58.0, 54.4, 53.2, 28.4, 28.3, 27.4, 25.7.
HRMS: observed—515.2880, calculated—515.2880.

Example 9

Di-tert-butyl ((1S, 2S)-cyclohex-3-ene-1, 2-diyl)dicarbamate (10)

To a solution of diboc compound 9 (300.00 mg, 0.58 mmol) in THF (5 mL) and ammonia (10 mL) at −78° C. was added sodium metal (428 mg, 18.75 mmol) portionwise and stirred at same temperature for 2 h. The reaction mixture was quenched with solid ammonium chloride and the reaction mass was brought to room temperature(27° C.). Water (10 mL) was added to the residue and compound was extracted with ethyl acetate (3×20 mL). The combined organic layer was dried over anhydrous Na$_2$SO$_4$, filtered and concentrated under reduced pressure to furnish a residue which was purified by column chromatography over silica gel, eluting with 10% ethyl acetate in pet ether as an eluent to afford compound 10 (173 mg, 91%) as a white solid.

R$_f$: 0.4 (Pet ether:ethyl acetate, 70:30).
MF: C$_{16}$H$_{28}$N$_2$O$_4$, MW: 312.41.
Yield: 91%.
$[\alpha]_D^{25}$: +12.5 (c 0.8, CHCl$_3$).
IR (CHCl$_3$, cm$^{-1}$): v$_{max}$ 3360, 2923, 1675, 1600, 1463, 1166.
MP: 135-137° C.

¹H NMR (500 MHz, CDCl₃+CCl₄): δ 5.81-5.70 (m, 1H), 5.48 (bd, J=10 Hz, 1H), 5.04 (bd, J=10 Hz, 1H), 4.74 (bd, J=10 Hz, 1H), 4.15-4.03 (m, 1H), 3.48 (bd, J=10 Hz, 1H), 2.34-1.93 (m, 4H), 1.44 (s, 9H), 1.43 (s, 9H).

¹³C NMR (125 MHz, CDCl₃+CCl₄): δ 156.5, 156.0, 129.5, 127.6, 79.5, 79.0, 53.2, 52.5, 28.6, 28.4, 24.8.

HRMS: Observed—335.1942, calculated—335.1940.

Example 10

Di-tert-butyl ((1R, 2R, 3S, 6S)-7-oxabicyclo-[4.1.0]-heptane-2, 3-diyl)dicarbamate (11)

To a cooled (0° C.) and stirred solution of diboc olefin 10 (90 mg, 0.29 mmol) in DCM (2 mL) was added NaH₂PO₄ (315 mg, 2.01 mmol) followed by m-CPBA (355 mg, 2.01 mmol). Reaction mixture was stirred at 0° C. for 30 min and then allowed to stir at room temperature(25° C.) for 6 h. After completion of the reaction, saturated aq. solution of Na₂S₂O₃ (3 mL) was added and the reaction mixture was further stirred for 30 min. Water (3 mL) was added to the reaction mixture and it was extracted with ethyl acetate (3×5 mL). The combined organic layer was washed with saturated aq. solution of NaHCO₃ (3 mL) and dried over anhydrous Na₂SO₄, filtered and concentrated under reduced pressure to furnish a residue which was purified by column chromatography over silica gel, eluting with 20% ethyl acetate in pet ether as an eluent to afford compound 11 (92 mg, 97%) as a white solid.

$R_f$: 0.4 (Pet. ether:ethyl acetate, 60:40).
MF: $C_{16}H_{28}N_2O_5$, MW: 328.41.
Yield: 97% (over two steps).
$[\alpha]_D^{25}$: +27.27 (c 1.1, CHCl₃).
IR (CHCl₃, cm⁻¹): $\nu_{max}$ 3359, 1681, 1519, 1168.
MP: 135-137° C.

¹H NMR (500 MHz, CDCl₃+CCl₄): δ 5.11 (bd, J=10 Hz, 1H), 4.87 (bs, 1H), 3.87-3.75 (m, 1H), 3.52 (bd, J=10 Hz, 1H), 3.27 (bs, 1H), 3.24 (bs, 1H), 2.11-1.88 (m, 3H), 1.81 (d, J=10 Hz, 1H), 1.46 (s, 9H), 1.42 (s, 9H).

¹³C NMR (125 MHz, CDCl₃+CCl₄): δ 156.5, 155.9, 79.7, 79.2, 56.1, 53.9, 53.4, 49.7, 28.6, 28.47, 28.44, 22.7.

HRMS: Observed—351.1890, calculated—351.1890.

Example 11

Di-tert-butyl (1R, 2R, 3S, 6S)-7-oxabicyclo-[4.1.0]-heptane-2, 3-diyldicarbamate (12)

To a stirred solution of epoxide 11 (60 mg, 0.18 mmol) in methanol (1 mL) was added diphenyl diselenide (4 mg, 0.01 mmol) followed by sodium borohydride (8 mg, 0.21 mmol) and reaction mixture was stirred at rt for 2 h. After disappearance of starting material which was monitored by TLC, THF (1 mL) was added followed by H₂O₂ (0.38 mL, 30%, 3.65 mmol) and it was further stirred for 1 h. The reaction mixture was concentrated; water was added and extracted with DCM (3×5 mL). The combined organic layer was dried over anhydrous Na₂SO₄, filtered and concentrated under reduced pressure to furnish a residue which was purified by column chromatography over silica gel, eluting with 20% ethyl acetate in pet ether as an eluent to afford allylic alcohol 12 (50 mg, 80%) as white solid.

$R_f$: 0.3 (Pet ether:ethyl acetate, 70:30).
MF: $C_{16}H_{28}N_2O_5$, MW: 328.41.
Yield: 80%.
$[\alpha]_D^{25}$: −41.25 (c 3.2, CHCl₃).
IR (CHCl₃, vmax 3430, 1679, 1645, 1528, 1366, 1163.
MP: 121-123° C.

¹H NMR (500 MHz, CDCl₃+CCl₄): δ 5.67 (bd, J=1.5 Hz, 1H), 5.54 (bd, J=5 Hz, 1H), 4.19-4.14 (m, 1H), 3.81-3.70 (m, 1H), 3.51-3.43 (m, 1H), 2.46 (dd, J=5, 15 Hz, 1H), 2.10-1.96 (m, 2H), 1.46 (s, 18H).

¹³C NMR (125 MHz, CDCl₃+CCl₄): δ 158.1, 156.7, 129.8, 124.7, 79.9, 73.5, 60.4, 48.8, 32.3, 28.3.

HRMS: Observed—351.1891, calculated—351.1890.

Example 12

Di-tert-butyl (1R, 2R, 3S, 6S)-7-oxabicyclo-[4.1.0] heptane-2, 3-diyldicarbamate (3)

To the solution of allylic alcohol 12 (25 mg, 0.07 mmol) in DCM (1 mL) was added NaHCO₃ (50 mg, 0.76 mmol) and Dess-Martin periodinate (85 mg, 0.22 mmol) at 0° C. The reaction mixture was stirred for overnight at rt. After completion of reaction, water (3 mL) was added to the reaction mass and compound was extracted with DCM (3×5 mL). The combined organic layer was dried over anhydrous Na₂SO₄, filtered and concentrated under reduced pressure to furnish a residue which was purified by column chromatography over silica gel, eluting with 10% ethyl acetate in pet. ether as an eluent to afford compound 3 (22 mg, 90%) as semisolid mass.

$R_f$: 0.4 (Pet. ether:ethyl acetate, 70:30).
MF: $C_{16}H_{26}N_2O_5$, MW: 326.39.
Yield: 90%.
$[\alpha]_D^{25}$: −114.9 (c 0.5, CHCl₃), lit. −116.3 (c 0.945, CHCl₃)
IR (CHCl₃, cm⁻¹): $\nu_{max}$ 3411, 2926, 1695, 1514, 1173.

¹H NMR (500 MHz, CDCl₃+CCl₄): δ 7.00-6.92 (m, 1H), 6.14 (dd, J=10.1 Hz, 3.1 Hz, 1H), 5.98 (d, J=7.3 Hz, 1H), 5.52 (d, J=6.1 Hz, 1H), 4.30 (dd, J=13.1, 6.4 Hz, 2H), 3.97-3.81 (m, 1H), 3.00-2.94 (m, 1H), 2.50-2.24 (m, 2H), 1.48 (s, 9H), 1.43 (s, 9H).

¹³C NMR (125 MHz, CDCl₃+CCl₄): δ 194.3, 157.7, 155.7, 148.4, 128.5, 80.4, 79.3, 60.5, 54.4, 34.6, 28.4, 28.3.

HRMS: Observed—349.0231, calculated—349.0236.

Example 13 to 18

Preparation of Oseltamivir Phosphate (1) from Intermediate (3) (Shibasaki et al; *J. Am. Chem. Society*, 2006, 128, 6312)

Example 13

(3R,4R,5S)-4,5-Bis(tert-butoxycarbonylamino)-1-cyano-3-hydroxycyclohexene(17)

A degassed solution of 3 (19.7 mg, 0.060 mmol), Ni(cod)$_2$ (1.7 mg, 0.006 mmol, 10 mol %), and 1,5-cyclooctadiene (0.1 M in THF, 60 µL, 0.006 mmol, 10 mol %) in THF (0.75 mL) was heated at 60° C. for 65 h. After filtration on celite pad to remove Ni(cod)$_2$, the filtrate was dissolved in THF and NBS (11.3 mg, 0.063 mmol, 1.05 equiv) was added at 4° C. (ice bath). After 20 min, Et$_3$N (0.12 mL, 0.85 mmol, 14 equiv) was added dropwise. After 40 min, toluene and 5% NaH$_2$PO$_4$ were added and the organic layer was separated. The product was extracted with toluene twice and the combined organic layer was dried over Na$_2$SO$_4$. Most of toluene was removed under reduced pressure (volume of mixture: ca. 1 mL). The resulting crude 16 was used in next step without purification. (β-Cyanoenone 16 was relatively unstable on silica gel column chromatography. However, 8 can be isolated in 71% yield.)

To a solution of LiAlH(OtBu)$_3$ (1 M in THF, 0.30 mL, 0.30 mmol, 5 equiv) in THF (2 mL), crude 16 (toluene solution) was added and the resulting mixture was stirred at 4° C. (ice bath). After 30 min, saturated aqueous NH$_4$Cl was added to quench the reaction. The product was extracted with AcOEt twice and the combined organic layer was washed with brine and dried over Na$_2$SO$_4$. The solvent was removed under reduced pressure and the residue was purified by column chromatography (silica gel, hexane-AcOEt, 2:1 to 3:2) to afford 17 (12.9 mg, 0.036 mmol) as a colorless solid in 60% yield (3 steps). The diastereoselectivity of the product was determined by 1H NMR analysis to be >20/1. If isolated 8 was used as a starting material, the yield of this reduction to give 17 was 94%.

Example 14

(3S,4R,5S)-5-tert-Butoxycarbonylamino-3,4-tert-butoxycarbonylimino-1-cyanocyclo hexene (18)

To a solution of PPh$_3$ (124 mg, 0.47 mmol, 2.5 equiv) in THF (6.3 mL), DEAD (40% in toluene, 0.22 mL, 0.47 mmol, 2.5 equiv) and 17 (66.9 mg, 0.19 mmol) in THF (3.1 mL) were added and the resulting mixture was stirred at 4° C. (ice bath). After 1 h, mixture was concentrated and purified by column chromatography (silica gel, hexane-AcOEt, 3:1 to 2:1) to afford 18 (55.4 mg, 0.17 mmol) as a colorless amorphous in 87% yield.

Example 15

(3R,4R,5S)-4,5-Bis(tert-butoxycarbonylamino)-1-cyano-3-(1-ethylpropoxy)cyclo hexene (19)

To a solution of 18 (22.6 mg, 0.067 mmol) in 3-pentanol (0.5 mL), BF$_3$.OEt$_3$ (0.1 M in 3-pentanol, 1 mL, 0.1 mmol, 1.5 equiv) was added dropwise and the resulting mixture was stirred at 4° C. (ice bath). After 1 h, saturated aqueous NaHCO$_3$ was added to quench the reaction. The product was extracted with AcOEt twice and the combined organic layer was washed with brine and dried over Na$_2$SO$_4$. The solvent was removed under reduced pressure and the residue was purified by column chromatography (silica gel, hexane-AcOEt, 4:1) to afford 19 (14.9 mg, 0.035 mmol) as a colorless solid in 52% yield.

Example 16

(3R,4R,5S)-4-Amino-5-tert-butoxycarbonylamino-1-cyano-3-(1-ethylpropoxy)cyclo hexene(20)

To a solution of 19 (96.3 mg, 0.23 mmol) in CH$_2$Cl$_2$ (5 mL), TFA (340 µL, 4.55 mmol, 20 equiv) was added at 4° C. (ice bath). After stirring at room temperature(30° C.) for 3 h, the reaction mixture was concentrated in vacuo and then, diluted with CH$_2$Cl$_2$ (5 mL). After cooling to 4° C., Et$_3$N (160 µL, 1.14 mmol, 5 equiv) and Boc$_2$O (55.3 mg, 0.25 mmol, 1.1 equiv) were added dropwise. After 30 min, the mixture was concentrated and purified by column chromatography (silica gel, hexane-AcOEt, 2:1 to 0:1) to afford 20 (46.6 mg, 0.14 mmol) as a colorless oil in 63% yield.

Example 17

(3R,4R,5S)-4-Acetoamide-5-tert-butoxycarbonylamino-1-cyano-3-(1-ethylpropoxy) cyclo hexene (21)

To a solution of 20 (46.6 mg, 0.14 mmol) in pyridine (2 mL), Ac$_2$O (27 µL, 0.28 mmol, 2 equiv) was added at room temperature(25° C.). After 1 h, the reaction mixture was directly concentrated in vacuo to remove pyridine. The residue was purified by column chromatography (silica gel, hexane-AcOEt, 4:1 to 1:1) to afford 21 (44.3 mg, 0.12 mmol) as a colorless solid in 84% yield.

Example 18

Ethyl(3R,4R,5S)-4-Acetamide-5-amino-3-(1-ethyl-propoxy)cyclohexene-1-carboxylate phosphate (1): (1) (Tamiflu®)

The solution of 21 (25.9 mg, 0.071 mmol) in 4.2 M HCl/EtOH was heated at 60° C. for 4 h. After cooling to 4° C. (ice bath), water was added to decompose the imino ester and the mixture was stirred for 3 h. CH$_2$Cl$_2$ was added followed by the slow addition of 2 M NaOH. The organic layer was separated and the product in water layer was extracted with CH$_2$Cl$_2$ twice and AcOEt once. The combined organic layer was washed with brine and dried over Na$_2$SO$_4$. A filtration and removal of solvent gave the free base (11.8 mg, 0.037 mmol) in 53% yield. To the solution of free base (10.4 mg, 0.033 mmol) in EtOH (250 µL), H$_3$PO$_4$ (1 M in EtOH, 33 µL, 0.033 mmol, 1 equiv) was added slowly and the mixture was warmed to 50° C. Crystallization commenced immediately. The suspension was cooled to room temperature(30° C.) and stirred for 1 h. The crystal was filtered and washed with acetone twice to afford Tamiflu (1) (6.9 mg, 0.017 mmol) as colorless crystal in 50% yield.

Advantages of Invention a. Trans isomer preferably synthesized
b. Avoids azide as well as aziridine
c. Abundant and cheap raw materials used
d. Utilises naturally occurring resources eg: Cysteine
e. First report of an intramolecular thiol and olefin cycloaddition in water
f. First report of its kind to show the application of Ramberg-Backlund reaction for tamiflu synthesis.

We claim:

1. A process for the preparation of an intermediate for the preparation of oseltamivir phosphate comprising the steps of:

a) providing allyl compound A from cysteine by a known method;

b) adding Zinc dust and saturated aq. solution of ammonium chloride to a solution of allyl compound A of step (a) in tetra hydro furan (THF) to obtain the reaction mixture;

c) refluxing the reaction mixture as obtained in step (b) to obtain thiol compound 5;

d) stirring the crude thiol 5 of step (c) at room temperature in the range of 25-30° C. in water to afford seven membered cyclic sulphide 7;

e) oxidising sulphide 7 of step (d) at room temperature in the range of 25-30° C. by oxone to afford sulfone 8;

f) subjecting sulfone 8 of step (e) to Ramberg-Backlund reaction to furnish the cyclohexene urea 4;

g) reducing urea 4 of step (f) with LAH to furnish imidazolidine and subjecting imidazolidine without purification to hydrolysis in 1% HCl to afford corresponding crude vicinal diamine;

h) masking the crude diamine of step (g) as its carbamate derivative with neat Boc anhydride to afford diboc 9;

i) subjecting compound 9 of step (h) to debenzylation under Birch conditions to obtain debenzylated compound 10;

j) epoxidation of compound 10 of step (i) furnishing α-carbamate directed stereospecific epoxide 11 as a single diastereomer;

k) rearranging epoxide 11 of step (j) to allylic alcohol 12 in one pot two steps protocol without isolation of the intermediate;

l) DMP oxidation of allylic alcohol 12 of step (k) on DMP in DCM affording an α, β-unsaturated ketone intermediate for the preparation of oseltamivir phosphate.

2. The process as claimed in claim 1, wherein refluxing in step c) is carried for 6 to 7 hrs.

3. The process as claimed in claim 1, wherein stirring in step d) is carried for 4 to 5 hrs.

\* \* \* \* \*